United States Patent
Buysse et al.

(10) Patent No.: US 8,211,099 B2
(45) Date of Patent: Jul. 3, 2012

(54) THERMAL FEEDBACK SYSTEMS AND METHODS OF USING THE SAME

(75) Inventors: Steven Paul Buysse, Longmont, CO (US); Casey M. Ladtkow, Arvada, CO (US); Brandon C. Gay, Superior, CO (US)

(73) Assignee: TYCO Healthcare Group LP, Mansfield, MA (US)

( * ) Notice: Subject to any disclaimer, the term of this patent is extended or adjusted under 35 U.S.C. 154(b) by 1190 days.

(21) Appl. No.: 12/023,606

(22) Filed: Jan. 31, 2008

(65) Prior Publication Data

US 2008/0183165 A1 Jul. 31, 2008

Related U.S. Application Data

(60) Provisional application No. 60/887,537, filed on Jan. 31, 2007.

(51) Int. Cl.
*A61B 18/18* (2006.01)
(52) U.S. Cl. .................. 606/34; 606/41; 606/42
(58) Field of Classification Search .............. 606/32–35
See application file for complete search history.

(56) References Cited

U.S. PATENT DOCUMENTS

| | | |
|---|---|---|
| 2,031,682 A | 2/1936 | Frederick et al. |
| 4,074,718 A | 2/1978 | Morrison, Jr. et al. |
| 4,075,497 A | 2/1978 | Kraus |
| 4,215,275 A | 7/1980 | Wickersheim |
| 4,375,220 A | 3/1983 | Matvias |
| 4,411,266 A | 10/1983 | Cosman |
| 4,448,547 A | 5/1984 | Wickersheim |
| 4,560,286 A | 12/1985 | Wickersheim |
| 4,565,200 A | 1/1986 | Cosman |
| 4,576,177 A | 3/1986 | Webster, Jr. |
| 4,608,977 A | 9/1986 | Brown |
| 4,662,383 A | 5/1987 | Sogawa et al. |
| 4,739,759 A | 4/1988 | Rexroth et al. |
| 4,752,141 A | 6/1988 | Sun et al. |
| 4,832,024 A | 5/1989 | Boussignac et al. |
| 4,880,719 A | 11/1989 | Murofushi et al. |

(Continued)

FOREIGN PATENT DOCUMENTS

DE 2407559 2/1974

(Continued)

OTHER PUBLICATIONS

Cosman ER, Cosman BJ: "Methods of Making Nervous System Lesions", in William RH, Rengachary SS (eds): Neurosurgery. New York: McGraw-Hill, vol. 111, pp. 2490-2498, 1984.

(Continued)

*Primary Examiner* — Linda Dvorak
*Assistant Examiner* — Amanda Scott

(57) ABSTRACT

A system for providing feedback during an electrosurgical procedure on a target tissue is provided. The system includes an electrosurgical energy source; an electrode probe assembly connected to the electrosurgical energy source, wherein the electrode probe assembly includes at least one electrode assembly having a needle configured to deliver electrosurgical energy to the target tissue; at least one thermal feedback assembly connected to the electrosurgical energy source, wherein each thermal feedback assembly includes at least one temperature sensor assembly; and a hub configured to selectively support the electrode probe assembly and each thermal feedback assembly such that the needle of the electrode probe assembly and each temperature sensor assembly of each thermal feedback assembly are proximate one another when disposed proximate the target tissue.

22 Claims, 6 Drawing Sheets

U.S. PATENT DOCUMENTS

| | | | |
|---|---|---|---|
| 4,883,354 A | 11/1989 | Sun et al. | |
| 4,961,435 A | 10/1990 | Kitagawa et al. | |
| 4,966,597 A | 10/1990 | Cosman | |
| 4,988,212 A | 1/1991 | Sun et al. | |
| 4,993,430 A | 2/1991 | Shimoyama et al. | |
| 5,029,588 A | 7/1991 | Yock et al. | |
| 5,103,804 A | 4/1992 | Abele et al. | |
| 5,225,741 A | 7/1993 | Auld et al. | |
| 5,230,623 A | 7/1993 | Guthrie et al. | |
| 5,233,515 A | 8/1993 | Cosman | |
| 5,246,438 A | 9/1993 | Langberg | |
| 5,267,994 A | 12/1993 | Gentelia et al. | |
| 5,281,213 A | 1/1994 | Milder et al. | |
| 5,323,778 A | 6/1994 | Kandarpa et al. | |
| 5,330,470 A | 7/1994 | Hagen | |
| 5,330,518 A | 7/1994 | Neilson et al. | |
| 5,334,193 A | 8/1994 | Nardella | |
| 5,342,357 A | 8/1994 | Nardella | |
| 5,348,554 A | 9/1994 | Imran et al. | |
| 5,370,675 A | 12/1994 | Edwards et al. | |
| 5,383,876 A | 1/1995 | Nardella | |
| 5,383,917 A | 1/1995 | Desai et al. | |
| 5,385,148 A | 1/1995 | Lesh et al. | |
| 5,403,311 A * | 4/1995 | Abele et al. | 606/49 |
| 5,409,000 A | 4/1995 | Imran | |
| 5,409,006 A | 4/1995 | Buchholtz et al. | |
| 5,417,686 A | 5/1995 | Peterson et al. | |
| 5,433,739 A | 7/1995 | Sluijter et al. | |
| 5,437,662 A | 8/1995 | Nardella | |
| 5,458,597 A | 10/1995 | Edwards et al. | |
| 5,462,521 A | 10/1995 | Brucker et al. | |
| 5,472,441 A | 12/1995 | Edwards et al. | |
| 5,490,850 A | 2/1996 | Ellman et al. | |
| 5,500,012 A | 3/1996 | Brucker et al. | |
| 5,520,684 A | 5/1996 | Imran | |
| 5,536,267 A | 7/1996 | Edwards et al. | |
| 5,571,147 A | 11/1996 | Sluijter et al. | |
| 5,588,432 A | 12/1996 | Crowley | |
| 5,599,345 A | 2/1997 | Edwards et al. | |
| 5,643,197 A | 7/1997 | Brucker et al. | |
| 5,647,871 A | 7/1997 | Levine et al. | |
| 5,662,111 A | 9/1997 | Cosman | |
| 5,683,384 A | 11/1997 | Gough et al. | |
| 5,688,267 A | 11/1997 | Panescu et al. | |
| 5,735,847 A | 4/1998 | Gough et al. | |
| 5,775,338 A | 7/1998 | Hastings | |
| 5,792,146 A | 8/1998 | Cosman | |
| 5,848,967 A | 12/1998 | Cosman | |
| 5,849,011 A | 12/1998 | Jones et al. | |
| 5,868,740 A | 2/1999 | LeVeen et al. | |
| 5,897,552 A * | 4/1999 | Edwards et al. | 606/31 |
| 5,921,982 A | 7/1999 | Lesh et al. | |
| 5,943,719 A | 8/1999 | Feldman et al. | |
| 5,951,546 A | 9/1999 | Lorentzen | |
| 6,001,093 A | 12/1999 | Swanson et al. | |
| 6,006,126 A | 12/1999 | Cosman | |
| 6,053,912 A | 4/2000 | Panescu et al. | |
| 6,059,780 A | 5/2000 | Gough et al. | |
| 6,061,551 A | 5/2000 | Sorrells et al. | |
| 6,074,389 A | 6/2000 | Levine et al. | |
| 6,080,149 A | 6/2000 | Huang et al. | |
| 6,080,150 A | 6/2000 | Gough | |
| 6,106,524 A | 8/2000 | Eggers et al. | |
| 6,113,591 A * | 9/2000 | Whayne et al. | 606/34 |
| 6,132,426 A | 10/2000 | Kroll | |
| 6,146,380 A | 11/2000 | Racz et al. | |
| 6,162,216 A | 12/2000 | Guziak et al. | |
| 6,203,541 B1 | 3/2001 | Keppel | |
| 6,241,725 B1 | 6/2001 | Cosman | |
| 6,246,912 B1 | 6/2001 | Sluijter et al. | |
| 6,277,116 B1 * | 8/2001 | Utely et al. | 606/42 |
| 6,287,305 B1 | 9/2001 | Heim et al. | |
| 6,306,132 B1 | 10/2001 | Moorman et al. | |
| 6,337,998 B1 | 1/2002 | Behl et al. | |
| 6,432,070 B1 | 8/2002 | Talish et al. | |
| 6,478,793 B1 | 11/2002 | Cosman et al. | |
| 6,500,172 B1 | 12/2002 | Panescu et al. | |
| 6,506,189 B1 | 1/2003 | Rittman, III et al. | |
| 6,530,922 B2 | 3/2003 | Cosman et al. | |
| 6,569,159 B1 | 5/2003 | Edwards et al. | |
| 6,575,969 B1 * | 6/2003 | Rittman et al. | 606/41 |
| 6,587,731 B1 * | 7/2003 | Ingle et al. | 607/101 |
| 6,605,085 B1 | 8/2003 | Edwards | |
| 6,613,047 B2 | 9/2003 | Edwards | |
| 6,685,729 B2 | 2/2004 | Gonzalez | |
| 7,137,980 B2 | 11/2006 | Buysse et al. | |
| 7,156,842 B2 | 1/2007 | Sartor et al. | |
| 7,179,255 B2 | 2/2007 | Lettice et al. | |
| 7,186,222 B1 | 3/2007 | Callister et al. | |
| 7,207,989 B2 | 4/2007 | Pike, Jr. et al. | |
| 7,218,958 B2 | 5/2007 | Rashidi | |
| 7,235,070 B2 | 6/2007 | Vanney | |
| 7,235,073 B2 | 6/2007 | Levine et al. | |
| 7,238,184 B2 | 7/2007 | Megerman et al. | |
| 7,264,619 B2 | 9/2007 | Venturelli | |
| 7,278,991 B2 | 10/2007 | Morris et al. | |
| 7,282,049 B2 | 10/2007 | Orszulak et al. | |
| 7,294,127 B2 | 11/2007 | Leung et al. | |
| 7,294,143 B2 | 11/2007 | Francischelli | |
| 7,302,285 B2 | 11/2007 | Fuimaono et al. | |
| 7,303,558 B2 | 12/2007 | Swanson | |
| 7,331,947 B2 | 2/2008 | McGuckin, Jr. et al. | |
| RE40,156 E | 3/2008 | Sharps et al. | |
| 7,341,586 B2 | 3/2008 | Daniel et al. | |
| 7,344,533 B2 | 3/2008 | Pearson et al. | |
| 7,364,578 B2 | 4/2008 | Francischelli et al. | |
| 7,364,579 B2 | 4/2008 | Mulier et al. | |
| 7,367,974 B2 | 5/2008 | Haemmerich et al. | |
| 7,367,975 B2 | 5/2008 | Malecki et al. | |
| 7,387,625 B2 | 6/2008 | Hovda et al. | |
| 7,419,486 B2 | 9/2008 | Kampa | |
| 7,419,487 B2 | 9/2008 | Johnson et al. | |
| 7,419,488 B2 | 9/2008 | Ciarrocca et al. | |
| 7,419,489 B2 | 9/2008 | Vanney et al. | |
| 7,422,587 B2 | 9/2008 | Bek et al. | |
| 2001/0001819 A1 | 5/2001 | Lee et al. | |
| 2001/0034518 A1 | 10/2001 | Edwards et al. | |
| 2002/0058933 A1 | 5/2002 | Christopherson et al. | |
| 2002/0111615 A1 * | 8/2002 | Cosman et al. | 606/41 |
| 2002/0120261 A1 | 8/2002 | Morris et al. | |
| 2002/0156472 A1 | 10/2002 | Lee et al. | |
| 2003/0018247 A1 | 1/2003 | Gonzalez | |
| 2003/0208193 A1 * | 11/2003 | Van Wyk | 606/34 |
| 2004/0002745 A1 | 1/2004 | Fleming et al. | |
| 2004/0039429 A1 | 2/2004 | Daniel et al. | |
| 2004/0181216 A1 | 9/2004 | Kelly et al. | |
| 2004/0199161 A1 | 10/2004 | Truckai et al. | |
| 2004/0254573 A1 | 12/2004 | Dycus | |
| 2004/0267256 A1 | 12/2004 | Garabedian et al. | |
| 2005/0096681 A1 | 5/2005 | Desinger et al. | |
| 2005/0107784 A1 | 5/2005 | Moses | |
| 2005/0107785 A1 | 5/2005 | Dycus | |
| 2005/0113824 A1 | 5/2005 | Sartor et al. | |
| 2005/0119655 A1 | 6/2005 | Moses | |
| 2005/0154387 A1 | 7/2005 | Moses | |
| 2005/0155743 A1 | 7/2005 | Getz, Jr. et al. | |
| 2005/0192564 A1 | 9/2005 | Cosman et al. | |
| 2006/0079885 A1 | 4/2006 | Rick et al. | |
| 2006/0079886 A1 * | 4/2006 | Orszulak et al. | 606/41 |
| 2006/0079887 A1 * | 4/2006 | Buysse et al. | 606/41 |
| 2007/0066971 A1 | 3/2007 | Podhajsky | |
| 2007/0073285 A1 | 3/2007 | Peterson | |
| 2007/0078453 A1 | 4/2007 | Johnson | |
| 2007/0078454 A1 | 4/2007 | McPherson | |
| 2007/0260240 A1 | 11/2007 | Rusin | |
| 2008/0021448 A1 | 1/2008 | Orszulak et al. | |
| 2008/0027424 A1 | 1/2008 | DeCarlo et al. | |
| 2008/0183165 A1 | 7/2008 | Buysse et al. | |

FOREIGN PATENT DOCUMENTS

| | | |
|---|---|---|
| DE | 10224154 | 12/2003 |
| EP | 0171967 A | 2/1986 |
| EP | 0246350 | 11/1987 |
| EP | 0310431 | 4/1989 |
| EP | 0608609 | 8/1994 |
| EP | 1070518 A2 | 1/2001 |
| EP | 1465037 A | 10/2004 |

| | | |
|---|---|---|
| EP | 1645234 | 4/2006 |
| EP | 1656900 | 5/2006 |
| FR | 2864439 | 7/2005 |
| WO | WO 93/24066 | 12/1993 |
| WO | WO 94/28809 | 12/1994 |
| WO | WO 96/04860 | 2/1996 |
| WO | WO 96/18349 | 6/1996 |
| WO | WO 96/29946 | 10/1996 |
| WO | WO 96/34571 | 11/1996 |
| WO | WO 96/39914 | 12/1996 |
| WO | WO 97/06739 | 2/1997 |
| WO | WO 97/06740 | 2/1997 |
| WO | WO 97/06855 | 2/1997 |
| WO | WO 97/17029 | 5/1997 |
| WO | WO 99/01074 | 1/1999 |
| WO | WO 99/04710 | 2/1999 |
| WO | WO 99/22657 | 5/1999 |
| WO | WO 00/67846 | 11/2000 |
| WO | WO 01/00114 A1 | 1/2001 |
| WO | WO 2004/045436 | 6/2004 |
| WO | WO 2005/009528 | 2/2005 |

OTHER PUBLICATIONS

Anderson, Gary et al., "A numerical study of rapid heating for high temperature radio frequency hyperthermia", International Journal of Bio-Medical Computing, 35 (1994) 297-307.
Goldberg, et al., "Tissue Ablation with Radiofrequency: Effective Probe Size, Gauge, Duration and Temperature and Lesion Volume", Acad Radio, 1995, vol. 2, No. 5, pp. 399-404.
Melvin A. Astrahan, "A Localized Current Field Hyperthermia System for Use with 192-Iridium Interstitial Implants", Medical Physics, 9(3), May/Jun. 1982.
Cosman et al. "Theoretical Aspects of Radiofrequency Lesions in the Dorsal Root Entry Zone". Neurosurgery 15:945-950, 1984.
Stuart W. Young, Nuclear Magnetic Resonance Imaging—Basic Principles, Raven Press, New York, 1984.
E.R. Cosman, et al., "Radiofrequency Lesion Generation and its Effect on Tissue Impedence", Applied Neurophysiology, 51:230-242, 1988.
K. Ogata, Modern Control Engineering, Prentice-Hall, Englewood Cliffs, N.J., 1970.
E. Alexander et al., "Magnetic resonance image-directed stereotactic neurosurgery: use of image fusion with computerized tomography to enhance spatial accuracy", J. Neurosurg., 83:271, 276, 1995.
Reidenbach (1995) "First Experimental Results with Special Applicators for High-Frequency Interstitial Thermotherapy", Society Minimally Ivasive Therapy, 4(Suppl 1) :40 (Abstr).
Organ LW. (1976) "Electrophysiologic Principles of Radiofrequency Lesion Making" Appl. Neurophysiol, vol. 39: pp. 69-76.
Livraghi et al. (1995) "Saline-enhanced RF Tissue Ablation in the Treatment of Liver Metastases", Radiology, 205-210.
Solbiati et al. (1995) "Percutaneous US-guided RF Tissue Ablation of Liver Metastases: Long-term Follow-up", Radiology, 197(P): 199.
Solbiati, et al. (2001) "Percutaneous Radio-frequency Ablation of Hepatic Metastases from Colorectal Cancer: Long-term Results in 117 Patients", *Radiology*, vol. 221, pp. 159-166.
Goldberg, et al., "Image-guided Radiofrequency Tumor Ablation: Challenges and Opportunities—Part I", (2001) *J Vasc. Interv. Radiol*, vol. 12, pp. 1021-1032.
McGahan et al. (1995) "Percutaneous Ultrasound-guided Radiofrequency Electrocautery Ablationof Prostate Tissue in Dogs", Acad Radiol, vol. 2, No. 1:pp. 61-65.
Goldberg et al. (1995) "Tissue Ablation with Radiofrequency Using Multiprobe Arrays", Acad Radiol, vol. 2: pp. 399-404.
Goldberg et al. (1995) "Saline-enhanced RF Ablation: Demonstration of Efficacy and Optimization of Parameter", Radiology, 197(P): 140 (Abstr).
Bulletin of the American Physical Society, vol. 47, No. 5, Aug. 2002.
European Search Report from Application EP 05021935 dated Jan. 27, 2006.
European Search Report from Application EP 05021939 dated Jan. 27, 2006,.
European Search Report from Application EP 05021025 dated Mar. 13, 2006.
European Search Report from Application EP 05021936.9 dated Feb. 6, 2006.
European Search Report from Application EP 05025423.4 dated Jan. 12, 2007.
European Search Report from Application EP 06019768 dated Jan. 8, 2007.
European Search Report from Application EP 05025424 dated Jan. 23, 2007.
European Search Report from Application EP 07009028 dated Jul. 16, 2007.
McRURY, Ian D., (2000) "The Effect of Ablation Sequence and Duration on Lesion Shape Using Rapidly Pulsed Radiofrequency Energy Through Electrodes", Springer Netherlands, vol. 4, No. 1, pp. 307-320.

* cited by examiner

US 8,211,099 B2

THERMAL FEEDBACK SYSTEMS AND METHODS OF USING THE SAME

CROSS-REFERENCE TO RELATED APPLICATIONS

The present disclosure claims the benefit of and priority to U.S. Provisional Application Ser. No. 60/887,537, filed on Jan. 31, 2007, the entire content of which is incorporated herein by reference.

BACKGROUND

1. Technical Field

The present disclosure relates to energy delivery feedback systems and, more particularly to thermal feedback systems for electrosurgical energy systems and methods of their use.

2. Background of Related Art

The use of electrical energy including radiofrequency and microwave energy ("RF & MW energy") and, in particular, radiofrequency electrodes or microwave antennae ("RF-electrodes/MW-antennae") for ablation of tissue in the body or for the treatment of pain is known. Generally, such RF electrodes (e.g., probes, resistive heating elements and the like) include an elongated cylindrical configuration for insertion into the body to target tissue which is to be treated or ablated. The RF electrodes can further include an exposed conductive tip portion and an insulated portion. The RF electrodes can also include a method of internal cooling (e.g., a Cool-tip™ or the like), such as the RF electrodes shown and described in U.S. Pat. No. 6,506,189 entitled "COOL-TIP ELECTRODE THERMOSURGERY SYSTEM" issued to Rittman, III et al., on Jan. 14, 2003 and U.S. Pat. No. 6,530,922 entitled "CLUSTER ABLATION ELECTRODE SYSTEM" issued to Cosman et al., on Mar. 11, 2003, the entire content of which is incorporated herein by reference. Accordingly, when the RF electrode is connected to an external source of radiofrequency power, e.g., an electrosurgical generator (device used to generate therapeutic energy such as radiofrequency (RE), microwave (MW) or ultrasonic (US)), and current is delivered to the RF electrode, heating of tissue occurs near and around the exposed conductive tip portion thereof, whereby therapeutic changes in the target tissue, near the conductive tip, are created by the elevation of temperature of the tissue.

In some applications, for example, tumor ablation procedures, multiple electrodes are inserted into the body in an array to enlarge ablation volumes.

In a particular application, arrays of high frequency electrodes are inserted into tumors. The electrodes are typically placed in a dispersed fashion throughout the tumor volume to cover the tumor volume with uniform heat. The multiple electrodes may be activated simultaneously or sequentially applied with high frequency energy so that each electrode heats the surrounding tissue. During series activation, energy is applied to each electrode one at a time. This sequence of cycling the energy through the electrodes continues at a prescribed frequency and for a period of time.

The electrode systems discussed above are limited by the practical size of lesion volumes they produce. Accordingly, electrodes with cooled conductive tips have been proposed. With cooling, radiofrequency electrode tips generally produce larger lesion volumes compared with radiofrequency electrodes, which are not cooled. For example, standard single cylindrical electrodes, with cooled tips, as described above, may make lesion volumes up to 2 to 3 cm in diameter in living tissue (e.g., the liver) by using needles of 1 to 2 mm in diameter and having exposed tip lengths of several centimeters.

SUMMARY

The present disclosure relates to thermal feedback systems for electrosurgical energy systems and methods of their use.

According to an aspect of the present disclosure, a system for providing feedback during an electrosurgical procedure on a target tissue is provided. The system includes an electrosurgical energy source; an electrode probe assembly connected to the electrosurgical energy source, wherein the electrode probe assembly includes at least one electrode assembly having a needle configured to deliver electrosurgical energy to the target tissue; at least one thermal feedback assembly connected to the electrosurgical energy source, wherein each thermal feedback assembly includes at least one temperature sensor assembly; and a hub configured to selectively support the electrode probe assembly and each thermal feedback assembly such that the needle of the electrode probe assembly and each temperature sensor assembly of each thermal feedback assembly are proximate one another when disposed proximate the target tissue.

The needle of the electrode probe assembly may include an electrically conductive distal tip electrically connected to the electrosurgical energy source.

The electrode probe assembly may be fluidly connected to a coolant supply and may be configured to receive a circulating fluid therein.

The thermal feedback assembly may include a one or more temperature sensors. Each temperature sensor may be oriented substantially parallel to an axis defined by the needle of the electrode probe assembly or protrude 90 degrees from the center exposed active electrode. The plurality of temperature sensors may be arranged in a linear array. The plurality of temperature sensors may be disposed on opposed sides of the needle of the electrode probe assembly. The plurality of temperature sensors may be uniformly spaced from one another. The plurality of temperature sensors may be arranged in one of a linear, rectilinear and a triangular array.

The system may further include a computer connected to at least one of the electrosurgical energy source, the electrode probe assembly and each thermal feedback assembly. In an embodiment, at least one of the electrosurgical or microwave generator, the electrode probe assembly and each thermal feedback assembly may transmit information to the computer, and wherein the computer performs an Arrhenius model calculation on the information received from the at least one of the electrosurgical energy source, the electrode probe assembly and each thermal feedback assembly.

The temperature sensors may include fiber optic temperature probes, thermisters, thermocouples or resistive temperature devices (RTD).

According to another aspect of the present disclosure, a method of performing a thermal treatment on a target tissue is provided. The method comprises the steps of providing an electrosurgical energy source; and providing a thermal feedback system. The thermal feedback system includes an electrode probe assembly connectable to the electrosurgical generator, wherein the electrode probe assembly includes at least one electrode assembly having a needle configured to deliver electrosurgical energy to the target tissue; at least one thermal feedback assembly connectable to the electrosurgical energy source, wherein each thermal feedback assembly includes at least one temperature sensor assembly; and a hub configured to selectively support the electrode probe assembly and each thermal feedback assembly such that the needle of the electrode probe assembly and each temperature sensor assembly of each thermal feedback assembly are proximate one another when disposed proximate the target tissue.

The method further includes the steps of inserting the needle of the electrode probe assembly and each temperature sensor of the thermal feedback assembly into a patient proximate the target tissue; activating the electrosurgical energy source for delivering electrosurgical energy to the target tissue via the needle of the electrode probe; and monitoring and transmitting changes in a characteristic of the target tissue to the electrosurgical energy source via the temperature sensors of the thermal feedback assembly.

The method may further include the step of performing an Arrhenius model calculation on the information received from each thermal feedback assembly.

The method may further include the step of selecting a particular electrode probe assembly for a particular thermal procedure or desired treatment size or volume. Size estimation may be accomplished prior to delivery of the electrode probe assembly. The method may further include the step of selecting a characteristic energy value to be delivered to the particular electrode probe assembly based on the characteristics of the electrode probe assembly and the characteristics of the target tissue to be treated.

The method may further include the step of providing feedback to the electrosurgical energy source from the plurality of thermal feedback probes. Size estimation may be conducted during energy activation.

The method may further include the step of providing a computer configured to receive information regarding characteristics of at least one of the target tissue, the feedback of energy delivery, the electrode probe assembly, the thermal feedback assembly and the electrosurgical energy source. The computer may be configured to receive feedback information from the thermal feedback assembly during a thermal treatment of the target tissue. The computer may be configured to perform an Arrhenius model calculation or other ablation size estimation on the information received from each thermal feedback assembly.

The method may further include the step of arranging the electrode probe assembly and each thermal feedback assembly in a linear array.

The method may further include the step of spacing the thermal feedback assemblies equally from each other and from the electrode probe assembly.

The method may further include the step of spacing the thermal feedback assemblies at a known or predetermined spacing.

The method may further include the step of circulating a fluid though the electrode probe assembly.

The method may further include the step of introducing the electrode probe assembly and each of the plurality of thermal feedback assemblies into the target tissue.

These and other aspects and advantages of the disclosure will become apparent from the following detailed description and the accompanying drawings, which illustrate by way of example the features of the disclosure.

BRIEF DESCRIPTION OF THE DRAWINGS

The features of the system and method of use of the system of the present disclosure will become more readily apparent and may be better understood by referring to the following detailed descriptions of illustrative embodiments of the present disclosure, taken in conjunction with the accompanying drawings, wherein.

DETAILED DESCRIPTION OF EMBODIMENTS

Figure 1:
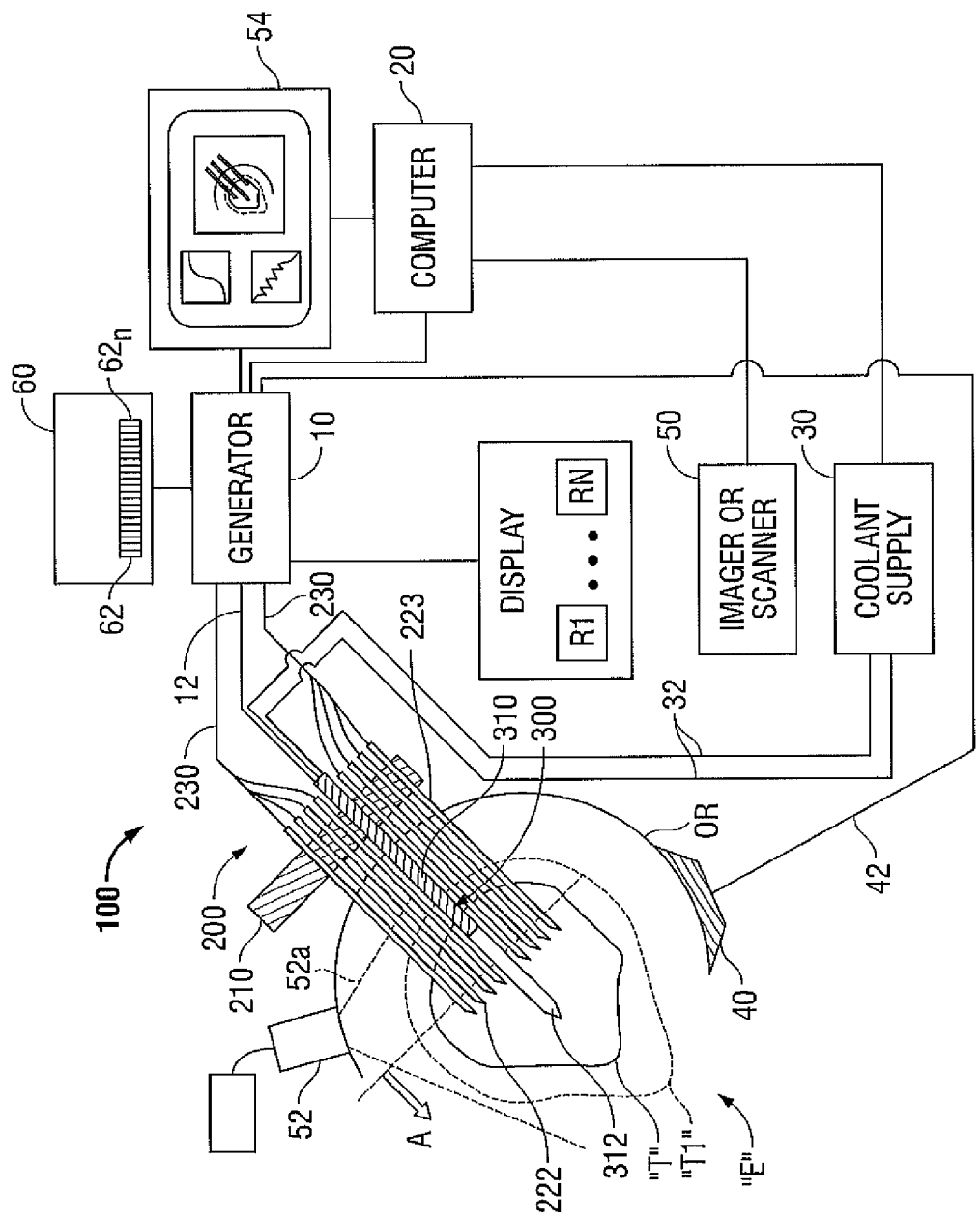
FIG. 1 is a schematic illustration of a thermal feedback system illustrating an electrode probe assembly and a thermal feedback assembly of the present disclosure operatively associated with a target surgical site.

The systems and methods of the present disclosure provide for a more precise controlled monitoring and/or feedback of an electrode probe during therapeutic use in a target surgical site, e.g., in a cancer tumor. Moreover, the systems and methods of the present disclosure provide for an improved ability to predict and/or estimate the depth and/or volume of treatment possible by the electrode probe when the electrode probe of an electrosurgical treatment device is set to a particular or various operative parameters.

It will be readily apparent to a person skilled in the art that the systems and methods of use of the systems can be used to monitor or provide feedback during treatment of body tissues in any body cavity or tissue locations that are accessible by percutaneous or endoscopic catheters or open surgical techniques, and is not limited to cancer tumors or the like. Application of the systems and methods in any corporal organ and/or tissue is intended to be included within the scope of the present disclosure.

1. System for Thermal Feedback

In the drawings and in the description which follows, the term "proximal", as is traditional, will refer to the end of the system, or component thereof, which is closest to the operator, and the term "distal" will refer to the end of the system, or component thereof, which is more remote from the operator.

With reference to FIG. 1, a thermal feedback system, according to an embodiment of the present disclosure, is generally designated as 100. Feedback system 100 includes a thermal feedback assembly 200 operatively connected to an electrosurgical generator and/or energy source 10 and/or computer 20.

At least one electrode probe assembly 300 is provided which is operatively associated with feedback assembly 200 and is connectable to electrosurgical energy source 10 in order to perform tissue ablation and the like. Each electrode probe assembly 300 may include a rigid shaft, antenna or needle 310 configured for insertion into a target tissue or organ "OR". Needle 310 of each probe assembly 300 may terminate in an exposed distal tip 312 having a pointed configuration for facilitating percutaneous insertion of needle 310 into body organ "OR". A portion of the external surface of needle 310 of each electrode probe assembly 300 is covered with an insulating material, as indicated by hatched line areas in FIG. 1. Distal tip 312 remains uncovered and is connected, through needle 310, to cable 12 and thereby to electrosurgical energy source 10. Electrode probe assembly 300 may include a coolant supply 30 fluidly connected to needle 310 for circulating a fluid thereto via conduit(s) 32.

Reference may be made to commonly assigned U.S. application Ser. No. 11/495,033, filed on Jul. 28, 2006, and entitled "COOL-TIP THERMOCOUPLE INCLUDING TWO-PIECE HUB" for a detailed discussion of the construction and operation of electrode probe assembly 300.

Temperatures at, or near the exposed distal tip(s) 312 of needle(s) 310 may be controlled by adjusting a flow of fluid coolant through needle 310. Accordingly, the temperature of the tissue contacting at or near distal tip(s) 312 is controlled. In operation, fluid from coolant supply 30 is carried the length of needle 310 through an inner tube (not shown) extending therethrough to the distal end of needle 310 terminating in an open end or cavity (not shown) of distal tip 312. At the opposite end of needle 310, the inner tube is connected to receive fluid. Backflow from distal tip(s) 312 is through an exit port (not shown) of needle 310.

Feedback system 100 may further include a reference electrode 40 that may be placed in contact with the skin of a patient or an external surface of organ "OR" with a connection 42 to electrosurgical energy source 10. Reference electrode 40 and connection 42 serve as a path for return current from electrosurgical energy source 10 through needle 310 of electrode probe assembly 300.

As seen in FIG. 1, by way of illustration only, a targeted region to be ablated is represented in sectional view by the line "T". It is desired to ablate the targeted region "T" by fully engulfing targeted region "T" in a volume of lethal heat elevation. The targeted region "T" may be, for example, a tumor which has been detected by an image scanner 50. For example, CT, MRI, fluoroscopy or ultrasonic image scanners may be used, and the image data transferred to computer 20. As an alternate example, an ultrasonic seamier head 52 may be disposed in contact with organ "OR" to provide an image illustrated by lines 52a.

For example, in FIG. 1, dashed line "T1" represents the ablation isotherm in a sectional view through organ "OR". Such an ablation isotherm may be that of the surface achieving possible temperatures of approximately 50° C. or greater. At that temperature range, sustained for approximately 30 seconds to approximately several minutes, tissue cells will be ablated. The shape and size of the ablation volume, as illustrated by dashed line "T1", may accordingly be controlled by a configuration of the electrode probe assemblies 300 used, the geometry of distal tips 312 of electrode probe assemblies 300, the amount of RF power applied, the time duration that the power is applied, the cooling of the needles 310 of electrode probe assemblies 300, etc.

Data processors may be connected to display devices to visualize targeted region "T" and/or ablation volume "T1" in real time during the ablation procedure.

As seen in FIG. 1, feedback system 100 may further include a library 60 including a plurality of thermal profiles/overlays $62_n$. As used herein, the term library is understood to include and is not limited to repository, databank, database, cache, storage unit and the like. Each overlay 62 includes a thermal profile which is characteristic of and/or specific to a particular configuration of cannula/electrode assembly or amount of exposure (i.e., specific to the length of exposure of distal tip 312 of needle 310 or the amount of needle 310 extending from a distal tip of a cannula) of the cannula/electrode assembly. In addition, for each amount of exposure or configuration of the cannula/electrode assembly, a plurality of overlays 62, is provided which includes a thermal profile which relates to, for example, the amount of time electrode probe assembly 300 is activated, to the temperature to which electrode probe assembly 300 is heated, etc.

With continued reference to FIG. 1, feedback system 100, as mentioned above, includes a thermal feedback assembly 200 operatively connected to an electrosurgical generator 10 and/or computer 20. Thermal feedback assembly 200 is operatively associated with the at least one electrode probe assembly 300.

As seen in FIG. 1, feedback assembly 200 includes a hub or housing 210 configured to selectively support at least one electrode probe assembly 300 and at least one temperature sensor assembly 220. As seen in FIG. 1, a plurality of temperature sensor assemblies 220 are shown supported in housing 210 on opposed sides of a single electrode probe assembly 300. It is contemplated that any number of temperature sensor assemblies 220 may be disposed on a single side, on opposed sides, or on multiple sides of the single electrode probe assembly 300 or relative to multiple electrode probe assemblies 300. It is further contemplated that multiple temperature sensor assemblies 220 may be interspersed amongst multiple electrode probe assemblies 300. Individual needles, cannula or introducers 223 may be used to introduce temperature sensors 222 into the target site or organ "OR".

Figure 2:
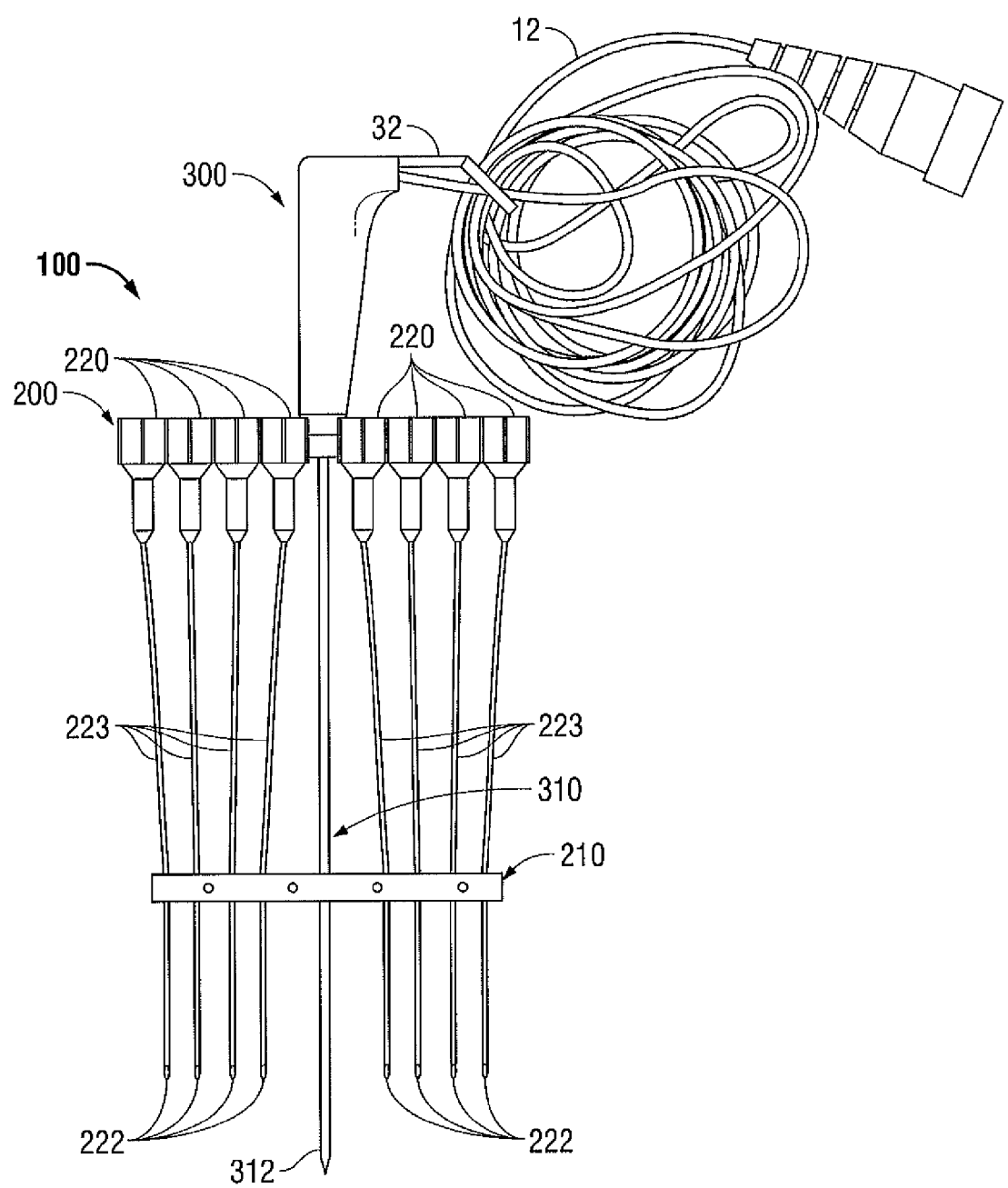
FIG. 2 is an illustration of the thermal feedback system of FIG. 1.

As seen in FIG. 2, housing 210 is used to position temperature sensor assemblies 220 on opposed sides of a singe electrode probe assembly 300 so as to define a single axis or plane. Housing 210 may be configured to position cannula 223 and temperature sensors 222 of temperature sensor assemblies 220 at a known distance from electrode probe assembly 300 and/or from one another, or are equi-distant or uniformly spaced from one another.

Figure 2A:
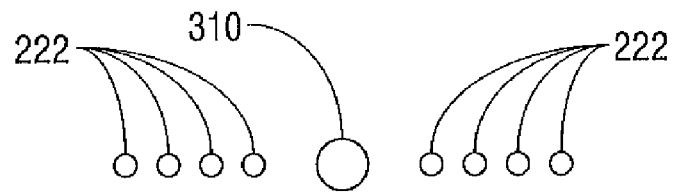
FIG. 2A is a schematic distal end view of the thermal feedback system of FIG. 2, illustrating the temperature array in a linear arrangement.
Figure 2B:
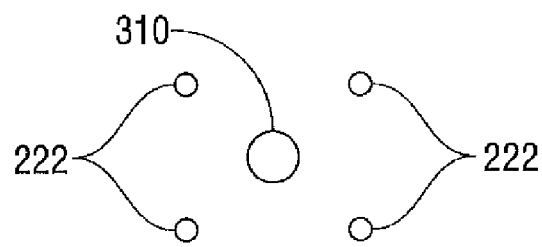
FIG. 2B is a schematic distal end view of an alternate arrangement of the thermal feedback system of FIG. 2, illustrating the temperature array in a rectangular arrangement.
Figure 2C:
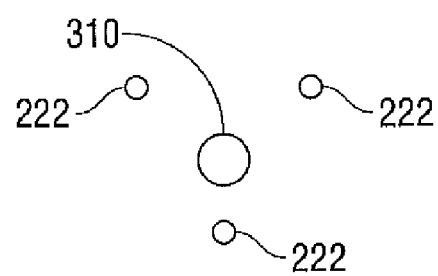
FIG. 2C is a schematic distal end view of a further alternate arrangement of the thermal feedback system of FIG. 2, illustrating the temperature array in a triangular arrangement.
Figure 2D:
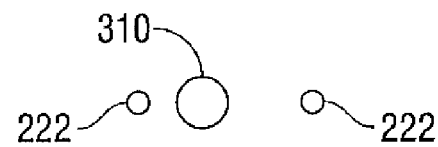
FIG. 2D is a schematic distal end view of the thermal feedback system of FIG. 2, illustrating the temperature array in an alternate linear arrangement.
Figure 3:
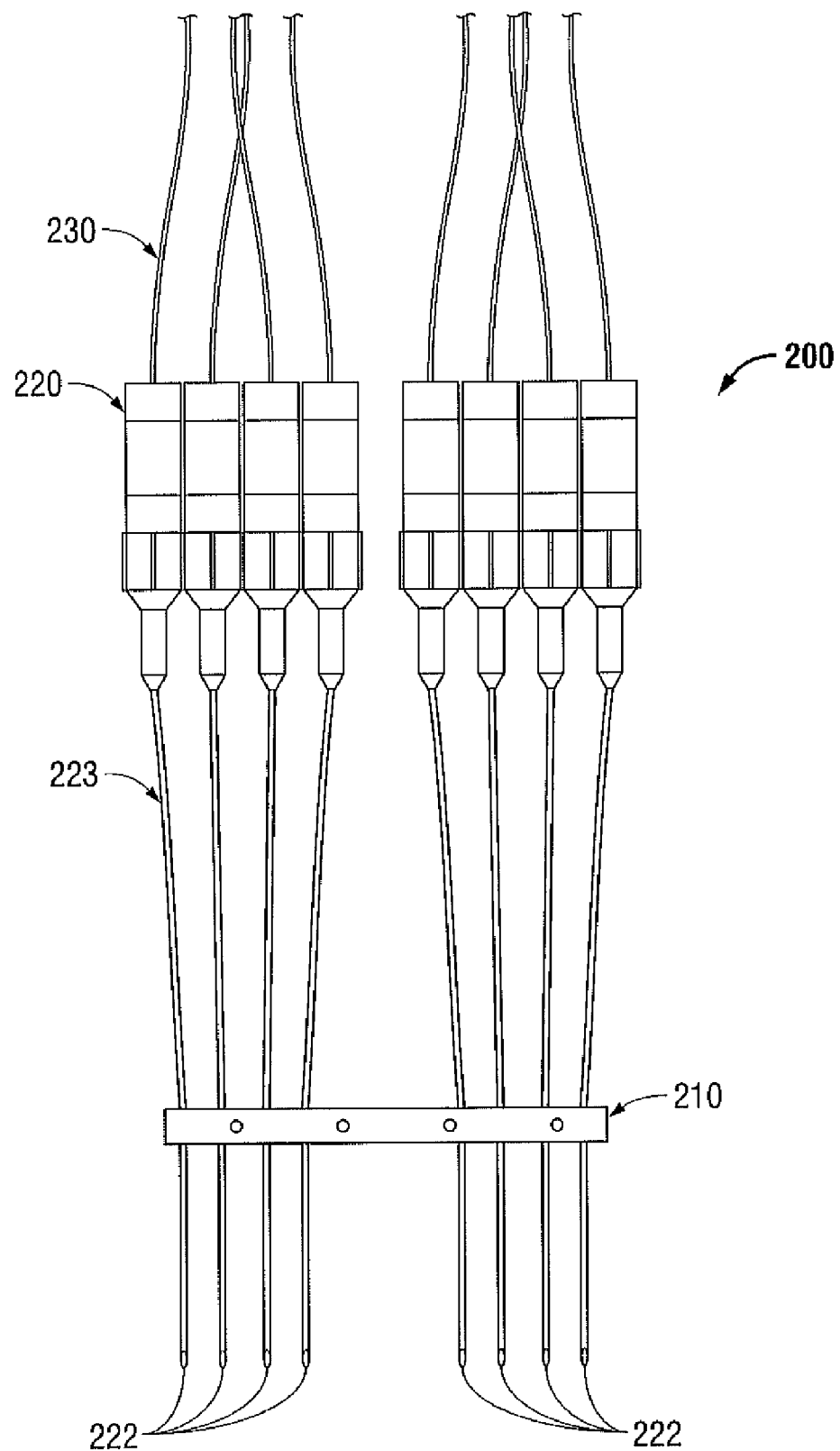
FIG. 3 is an illustration of a feedback/monitoring assembly of the thermal feedback system.
Figure 4:
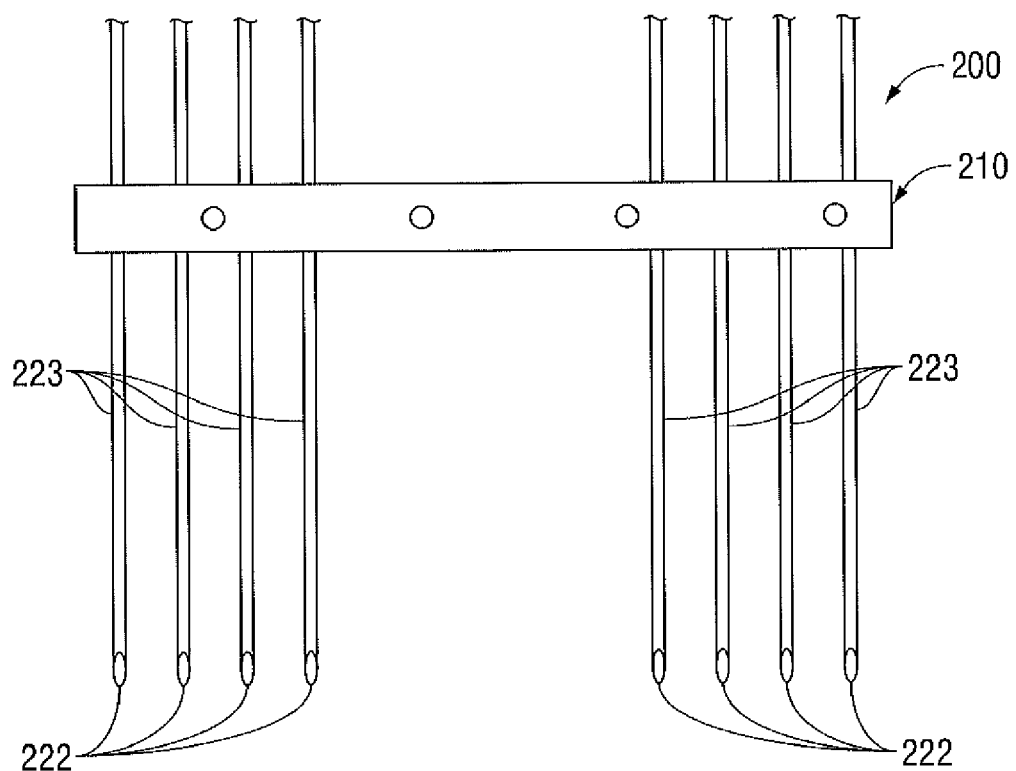
FIG. 4 is an enlarged view of the indicated area of detail of FIG. 3.

As seen in FIG. 2A, temperature sensors 222 and electrode assembly 310 are arranged in a linear array. As seen in FIG. 2B, temperature sensors 222 and electrode assembly 310 may be arranged in a rectilinear array. As seen in FIG. 2C, temperature sensors 222 and electrode assembly 310 may be arranged in a triangular array. As seen in FIG. 2D, temperature sensors 222 are arranged at a known distance from electrode assembly 310. As seen in FIGS. 2-2D, electrode assembly 310 is located at the center of temperature sensors 222; however, electrode assembly 310 may be located at any position relative to sensors 222.

Each temperature sensor assembly 220 is electrically or optically connected to electrosurgical generator 10 via a suitable electrical connector or the like 230.

Temperature sensors 222 include one or more of an emitter, sensor or marker to provide spatial relationship to electrode assembly 310. Each temperature sensor assembly 220 may include a temperature sensor 222 in the form of a rigid or semi-rigid cannula 223 and/or needles configured for insertion and/or penetration into the target surgical site. Suitable temperature sensors 222 may include thermocouples, resistive temperature devices (RTD) or fiber optic temperature probes sold under the tradename "Fluoroptic® Thermometer, available from Luxtron®, Santa Clara, Calif. Temperature sensors 222 are shown and described in U.S. Pat. Nos. 4,075,497; 4,215,275; 4,448,547; 4,560,286; 4,752,141; 4,883,354; and 4,988,212.

Fluoroptic® temperature sensors 222 are configured to measure the decay time of light emitted from phosphorescent materials (e.g., phosphors). The decay time is a persistent property of the sensor that varies directly with the temperature.

Other suitable temperature sensors for use with temperature sensor assemblies 220, to measure the temperature at a target surgical site, include and are not limited to optical sensors (e.g., Flouroptic®, infrared, etc.), thermocouples, Resistance-Temperature-Detectors (RTD), thermistors, MRI, fluoroscopic, ultrasound, CT and the like.

Temperature sensors 222 may be configured to measure or monitor temperatures greater than about 60° C. In an embodiment, feedback system 100 may be provided with suitable algorithms or the like for interpolating temperature values from at least two temperature sensors 222 and/or for integrating thermal damage from at least two temperature sensors 222. One real-time temperature sensor may be used in conjunction with an assumed or predetermined value from a look-up table or similar method.

The temperature measurements delivered to feedback system 100 may be used to generate a thermal map of the target area and/or, upon integration, may be used to account for particular tissue characteristics, such as, for example, perfusion, conduction, resistance and/or density.

Figure 7A:
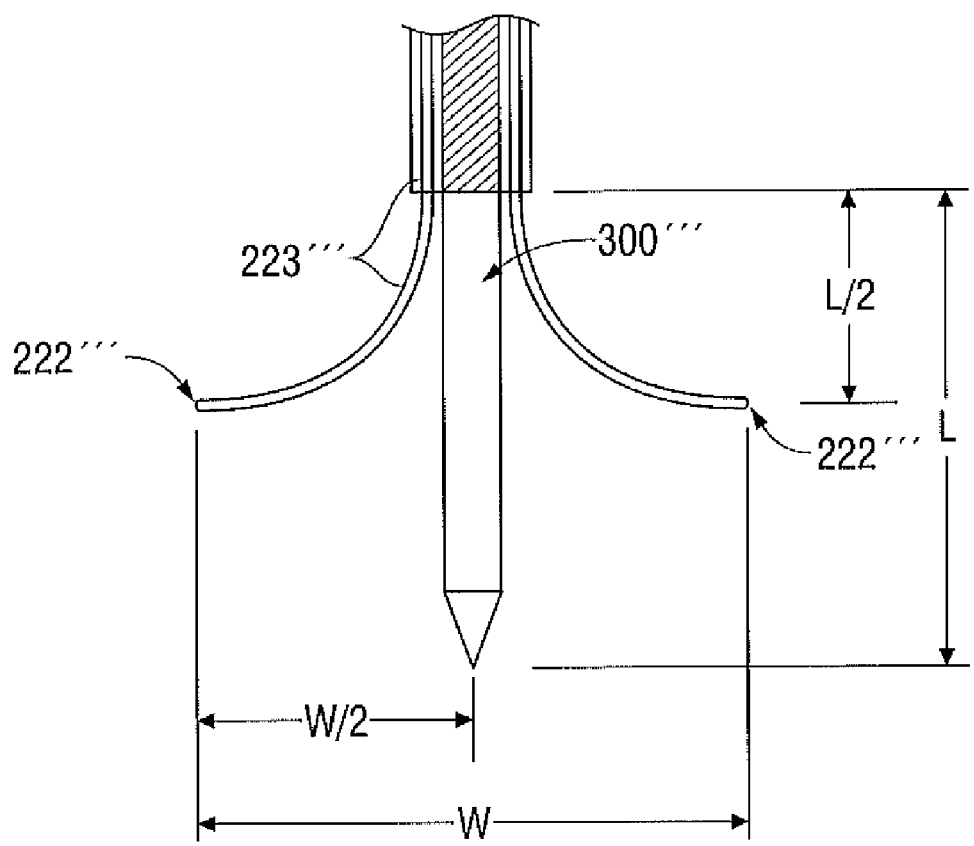
FIG. 7A is a schematic illustration of a distal end of an electrode probe according to an embodiment of the present disclosure.
Figure 7B:
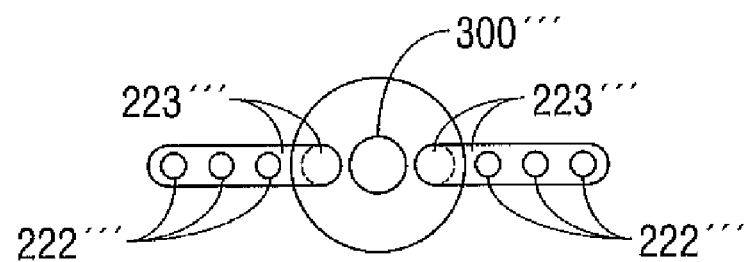
FIG. 7B is a distal, elevational view of the electrode probe of FIG. 7A.

In an embodiment, temperature sensors 222 may be deployed around needle 310 of the electrode probe assembly 300. Such temperature sensors may be constructed of suitable shape memory alloys so as to permit the temperature sensor to wrap around needle 310. Additionally, in an embodiment, a cannula including temperature sensors may be deployed about needle 310 of the electrode probe assembly 300. In another embodiment, as seen in FIGS. 7A and 7B, temperature sensors 222 may protrude at a substantially right angle from a center or mid point of the exposed distal tip 312 of needle 310.

Electrosurgical generator 10 and electrode probe assembly 300 may be configured to deliver energy to at least one of a radiofrequency, a microwave, an ultrasound, and a cryotherapy needle.

Feedback system 100 is capable of providing size predictability for ablation volume to be created during a thermal procedure of a target region prior to the ablation volume exceeding a predetermined volume during the thermal procedure. For example, feedback system 100 may provide feedback regarding a volume of the thermal therapy (e.g., diameter), and estimation of an overall size of the volume of the thermal therapy, an estimation of a rate of growth of the volume of the thermal therapy, and/or an estimation of a time to completion of the thermal therapy. All of this information may be displayed on a monitor 54 (See FIG. 1) or the like. Additionally, monitor 54 may illustrate the growth of the ablation volume, in real-time, as the procedure is going forward.

Figure 5:
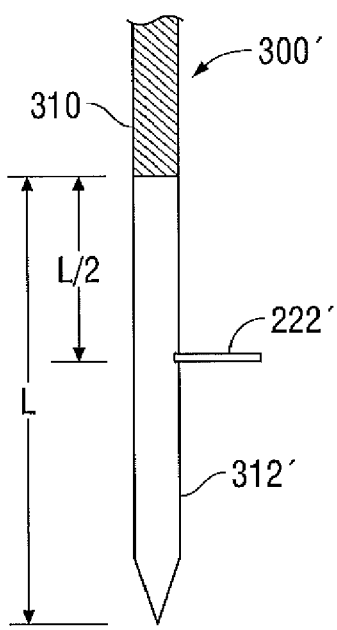
FIG. 5 is a schematic illustration of a distal end of an electrode probe assembly according to a further embodiment of the present disclosure.
Figure 6:
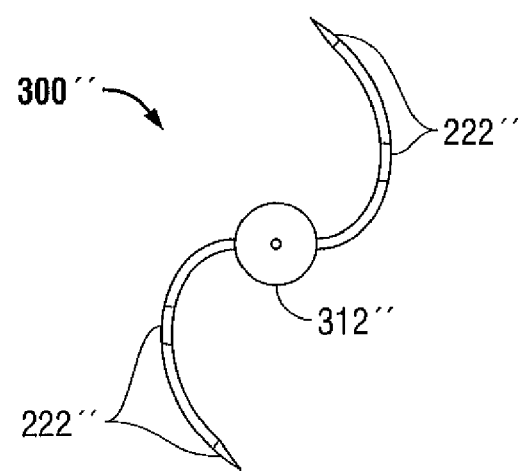
FIG. 6 is a distal end view of an electrode probe assembly similar to the electrode probe assembly of FIG. 5.

As seen in FIGS. 5-7, a distal end of electrode probe assemblies according to further embodiments of the present disclosure are generally designated as 300' and 300", respectively. Electrode probe assembly 300', 300'" is substantially similar to electrode probe assembly 300 and thus will only be discussed in further detail herein to the extent necessary to identify differences in construction and operation thereof.

As seen in FIGS. 5 and 7, distal tip 312' of electrode probe assembly 300' has a length of exposure "L". Additionally, electrode probe assembly 300' is configured such that temperature sensor 222' extends radially outward therefrom at a location approximately equal to "L/2". As seen in FIG. 5, temperature sensor 222' may extend radially and linearly from electrode probe assembly 300' (e.g., in a plane that is substantially orthogonal to a longitudinal axis of electrode probe assembly 300'), or, as seen in FIG. 6, temperature sensor 222" may extend radially and arcuately from electrode assembly 300" (e.g., in a plane that is substantially orthogonal to a longitudinal axis of electrode probe assembly 300").

As seen in FIG. 5, a single temperature sensor 222' may extend from electrode assembly 300', and as seen in FIG. 6, a pair of temperature sensors 222" may extend from electrode assembly 300". In any of the embodiments disclosed herein, any number of temperature sensors 222' or 222" may be used to extend from electrode assembly 300', 300" or 300'".

Each temperature sensor 222' or 222" may include at least one, and as seen in FIGS. 5 and 6, a plurality of discrete respective temperature sensor elements 222a', 222a" disposed along a length thereof, such as, for example, at least at a tip thereof, at a mid-point thereof and at a base or proximal end thereof.

As seen in FIGS. 5 and 6, each temperature sensor 222' or 222" may be slidably disposed within a respective electrode probe assembly 300', 300" and configured so as to project and/or retract from within electrode probe assembly 300' or 300". Each temperature sensor 222', 222" may extend along an outer surface of a respective electrode probe assembly 300', 300".

Each temperature sensor 222', 222" may be deployable to a known and/or predetermined radial distance from respective distal tips 312', 312" of respective electrode probe assembly 310', 310". In accordance with FIG. 6, or in embodiments employing multiple temperature sensors 222", the multiple temperature sensors 222" may be deployed to a known and/or predetermined distance from one another.

As seen in FIG. 7, temperature sensors 222'" may be disposed to a known and/or predetermined radial distance from electrode probe assembly 300'". Temperature sensors 222'" are generally disposed L/2 and ½ desired diameter of thermal ablation (W/2), wherein "L" is the length of exposure of the distal end of electrode probe assembly 300'" and "W" is the approximate diameter of the thermal ablation.

2. Method for Thermal Feedback

With reference to FIGS. 1-7B, a method of using thermal feedback system 100 during the thermal treatment of a target tissue or organ "OR" with electrode probe assembly 300, 300' or 300", in conjunction with hyperthermia feedback assembly 200, is described.

A method of the present disclosure includes determining a zone of thermal treatment during and/or post treatment of the target tissue or organ "OR". The method may comprise the step of measuring a temperature of the target tissue or organ "OR", at known distances relative thereto, during and/or post treatment of the target tissue or organ "OR". The temperature of the target tissue or organ "OR", at the known distance, may be an absolute temperature and/or a temperature that is interpolated. Additionally, the method may comprise integrating the temperature over time to determine an extent of thermal treatment. Such an integration may be calculated using an "Arrhenius thermal treatment integral" or other methods of thermal damage estimation.

As used herein, "thermal damage" is a term that describes a quantity representing a relative amount of destruction to a tissue component. The component of interest can vary widely between applications from sub-cellular components, such as, for example, protein or organelles, to many celled systems, such as, for example, tumors or organs. To study systems spanning such a wide range of scale different techniques may be applied. For a relatively small system, one approach may be an "ab initio" method or some other molecular dynamic approach. For relatively larger systems, one approach may be to use an empirical method, such as, for example, the "Arrhenius" method described herein or a critical temperature criterion.

The term "Arrhenius thermal treatment" refers to a method of quantifying thermal effects on underlying tissue. The present method thus models microscopic effects in tissue, such as, for example, the denaturation of a single species of protein, or models macroscopic effects in tissue, such as, for example, a color change of the tissue associated with the thermal treatment where many different reactions have taken place.

The equation for the "Arrhenius model" may be represented by the following equation:

$$\Omega(t) = -\ln\left(\frac{c(t)}{c(o)}\right) = A \int_0^\tau e^{\left(\frac{-\Delta E}{RT}\right)} dt$$

where:
$\Omega$=is the thermal effect sustained by the tissue or organ;
$c(t)$=is the amount of the component of interest remaining;
$c(0)$=is the amount of the component of interest at time zero;
$A$=is the frequency factor, approximately $7.39 \times 10^{39}$ 1/s (specific to liver tissue); and
$\Delta E$=is the activation energy, approximately $2.577 \times 10^5$ J/mol (specific to liver tissue).

The "Arrhenius model" is used because, in addition to combined processes, the "Arrhenius model" applies to individual processes as well. Individual processes that may be of interest include and are not limited to the denaturation of a lipid bi-layer of a cell, the denaturation of mitochondrial proteins, and the denaturation of nuclear proteins. The denaturation of lipid bi-layer is of interest because the lipid bi-layer loses its structure before many other parts of a cell. The denaturation of mitochondrial and nuclear proteins is of interest because they denature at temperatures in the range of about 42 to 60° C.

A method of the present disclosure may also include the step of using a position of electrode probe assembly 300, 300' or 300', and needle 310, positional temperature and/or feedback temperature received from hyperthermia feedback assembly 200 to determine the extent of thermal effect or treatment to the target tissue or organ "OR". The position of electrode probe assembly 300, 300' or 300" and needle 310 may be determined using a suitable positional indicator. The positional temperature may be determined by the location of temperature sensor 222, 222', 222' or 222''' and may be used to determine the presence of the lack of heat in the tissue or organ "OR".

A method of the present disclosure may also include the step of determining the spatial relationship between electrode probe assembly 300 and temperature sensor 222. Spatial relationship of electrode probe assembly 300 and temperature sensor 222 and temperature measured at temperature sensor 222 are feedback to computer 20 to determine an extent of thermal damage that may be displayed on monitor 54 or used to alter the output of electrosurgical energy source 10.

A method of the present disclosure may use a three-dimensional (3D) thermal image/map to determine a dimension of thermal treatment of the target tissue of organ "OR".

According to a method of the present disclosure, computer 20 of feedback system 100 is provided with information regarding a location of the target tissue or organ "OR", a location of critical biological structures (e.g., tissue, organs, vessels, etc.), a size and/or shape of the tumor or the target tissue or organ "OR" to be thermally treated, and a desired size of the thermal treatment volume. With this information inputted into computer 20, computer 20 may apply the "Arrhenius model" in order to develop a course of treatment.

According to a method of the present disclosure, an electrode probe assembly 300, 300' or 300" including a particular needle 310 having a given length "L" of exposure of distal tip 312 thereof is selected for a particular thermal procedure. A length "L" of electrode exposure may be user selected based on a desired volume of tissue to be treated or diameter "W" of thermal treatment. With the particular electrode probe assembly 300, 300' or 300" selected the parameters (e.g., dimensions, power rating, etc.) of electrode probe assembly 300, 300' or 300" is manually inputted or automatically selected from a look-up table for use by the electrosurgical generator 10 and/or computer 20.

With the parameters or characteristics of the tumor, target tissue or organ "OR" inputted into the electrosurgical energy source 10 and/or computer 20 and the parameters or characteristics of the electrode probe assembly 300, 300' or 300" selected also inputted into the electrosurgical generator 10 and/or computer 20, the parameters of the energy to be delivered to the tumor, target tissue or organ "OR", via the electrode probe assembly 300, 300' or 300", are determined. As seen in FIG. 1, with the parameters of the energy to be delivered determined, thermal feedback assembly 200 and with electrode probe assembly 300 inserted into the patient, proximate the tumor, target tissue or organ "OR". In particular, temperature sensors 222 of thermal feedback assembly 200 and needle 310 of electrode probe assembly 300 may be inserted into the tumor, target tissue or organ "OR".

With thermal feedback assembly 200 and electrode probe assembly 300 positioned, the placement of thermal feedback assembly 200 and electrode probe assembly 300 is confirmed. Next, a spatial relationship of temperature sensors 222 and electrode probe assembly 300 may be determined by using thermal feedback assembly 200 or use of other markers, and communicated to electrosurgical energy source 10 and/or computer 20 for use of feedback control of energy parameter and/or size estimation. After confirmation of the placement of thermal feedback assembly 200 and electrode probe assembly 300 the thermal treatment of the tumor, target tissue or organ "OR" may begin. The thermal treatment of the tumor, target tissue or organ "OR" includes delivering energy produced by electrosurgical generator 10 to the tumor, target tissue or organ "OR" via electrode probe assembly 300.

During the thermal treatment of the tumor, target tissue or organ "OR" hyperthermia feedback assembly 200 provides feedback to electrosurgical energy source 10 and/or computer 20 in the manner described above. Treatment progress is determined by computer 20 with feedback from at least one of image scanner 5, electrosurgical energy source 10, and temperature sensors 222. Treatment progress is displayed on monitor 54. Treatment progress includes one of size estimation, rate of treatment progression, and relationship of treatment volume to target volume.

While the above description contains many specific examples, these specific should not be construed as limitations on the scope of the disclosure, but merely as exemplifications of preferred embodiments thereof. Those skilled in the art will envision many other possible variations that are within the scope and spirit of the disclosure as defined by the claims appended hereto.

What is claimed is:

1. A system for providing feedback during an electrosurgical procedure on a target tissue, the system comprising:
    an electrosurgical energy source;
    an electrode probe assembly connected to the electrosurgical energy source, the electrode probe assembly including at least one electrode assembly having a needle configured to deliver electrosurgical energy to the target tissue;

a thermal feedback assembly connected to the electrosurgical energy source, the thermal feedback assembly including at least one temperature sensor assembly; and a hub configured to selectively support the electrode probe assembly and the thermal feedback assembly such that the needle of the electrode probe assembly and each temperature sensor assembly of the thermal feedback assembly are proximate to one another when disposed proximate the target tissue.

2. The system according to claim 1, wherein the needle of the electrode probe assembly includes an electrically conductive distal tip electrically connected to the electrosurgical energy source.

3. The system according to claim 1, wherein the needle of the electrode probe assembly includes a radiating distal tip electrically connected to the electrosurgical energy source.

4. The system according to claim 1, wherein the thermal feedback temperature sensors are disposed at a spatial relationship to the electrode probe assembly.

5. The system according to claim 1, wherein the thermal feedback assembly includes a plurality of temperature sensors, wherein each temperature sensor is oriented substantially parallel to an axis defined by the needle of the electrode probe assembly.

6. The system according to claim 5, wherein the plurality of temperature sensors are arranged in one of a linear, rectilinear and a triangular array.

7. The system according to claim 5, wherein the plurality of temperature sensors are arranged in a linear array.

8. The system according to claim 7, wherein the plurality of temperature sensors are disposed on opposed sides of the needle of the electrode probe assembly.

9. The system according to claim 8, wherein the plurality of temperature sensors are uniformly spaced from one another.

10. The system according to claim 1, wherein the thermal feedback assembly includes a plurality of temperature sensors, wherein each temperature sensor is oriented substantially orthogonal to an axis defined by the needle of the electrode probe assembly.

11. The system according to claim 1, further comprising a computer connected to at least one of the electrosurgical energy source, the electrode probe assembly and the thermal feedback assembly, wherein at least one of the electrosurgical energy source, the electrode probe assembly and the thermal feedback assembly transmits information to the computer, and wherein the computer performs at least one of:

an Arrhenius model calculation; and a determination of an ablation size based on reaching a predetermined temperature set point of about 60° C.;

on the information received from the at least one of the electrosurgical energy source, the electrode probe assembly and the thermal feedback assembly.

12. A method of performing a thermal treatment on a target tissue, comprising the steps of:

providing an electrosurgical energy source;

providing a thermal feedback system including:

an electrode probe assembly connectable to the electrosurgical energy source, the electrode probe assembly including at least one electrode assembly having a needle configured to deliver electrosurgical energy to the target tissue;

a thermal feedback assembly connectable to the electrosurgical energy source, the thermal feedback assembly including at least one temperature sensor assembly; and a hub configured to selectively support the electrode probe assembly and the thermal feedback assembly such that the needle of the electrode probe assembly and each temperature sensor assembly of the thermal feedback assembly are proximate to one another when disposed proximate the target tissue;

inserting the needle of the electrode probe assembly and each temperature sensor of the thermal feedback assembly into a patient proximate the target tissue;

activating the electrosurgical energy source for delivering electrosurgical energy to the target tissue via the needle of the electrode probe; and monitoring and transmitting changes in a characteristic of the target tissue to the electrosurgical energy source via the temperature sensors of the thermal feedback assembly.

13. The method according to claim 12, further comprising the step of performing an Arrhenius model calculation on the information received from the thermal feedback assembly.

14. The method according to claim 12, further comprising the step of selecting a characteristic energy value to be delivered to a particular electrode probe assembly based on the characteristics of the electrode probe assembly and the characteristics of the target tissue to be treated.

15. The method according to claim 12, further comprising the step of providing feedback to the electrosurgical energy source from the plurality of thermal feedback probes.

16. The method according to claim 12, further comprising the step of providing a computer configured to receive information regarding characteristics of at least one of the target tissue, the electrode probe assembly, the thermal feedback assembly and the electrosurgical energy source, the computer being configured to receive feedback information from the thermal feedback assembly during a thermal treatment of the target tissue, and the computer being configured to perform an Arrhenius model calculation on the information received from the thermal feedback assembly.

17. The method according to claim 14, further comprising the step of arranging the electrode probe assembly and the thermal feedback assembly in a linear array.

18. The method according to claim 17, further comprising the step of spacing the temperature sensor assemblies equally from each other and from the electrode probe assembly.

19. The method according to claim 17, further comprising the step of spacing the temperature sensor assemblies at known spatial distances from each other and from the electrode probe assembly.

20. The method according to claim 12, further comprising the step of deploying the temperature sensors at a known distance from the electrode assembly.

21. The method according to claim 12, further comprising the step of deploying the temperature sensor at substantially a right angle with respect to an axis of the electrode assembly.

22. The method according to claim 12, further comprising the step of deploying the temperature sensor substantially from a mid-point of an exposed portion of the electrode assembly.

* * * * *